(12) United States Patent
Hedrick et al.

(10) Patent No.: US 7,053,221 B2
(45) Date of Patent: May 30, 2006

(54) HETEROATOM-STABILIZED CARBENES AND PRECURSORS THERETO AS DEPOLYMERIZATION CATALYSTS

(75) Inventors: James Lupton Hedrick, Pleasanton, CA (US); Gregory Walker Nyce, San Jose, CA (US); Robert M. Waymouth, Palo Alto, CA (US)

(73) Assignee: International Business Machines Corporation, Armonk, NY (US)

( * ) Notice: Subject to any disclaimer, the term of this patent is extended or adjusted under 35 U.S.C. 154(b) by 226 days.

(21) Appl. No.: 10/355,554

(22) Filed: Jan. 30, 2003

(65) Prior Publication Data

US 2005/0049418 A1    Mar. 3, 2005

Related U.S. Application Data

(62) Division of application No. 10/330,853, filed on Dec. 26, 2002, now Pat. No. 6,911,546.

(51) Int. Cl.
*C07D 277/14*    (2006.01)

(52) U.S. Cl. .................. 548/181; 548/215; 548/316.7; 558/80

(58) Field of Classification Search ............. 548/181, 548/215, 316.7; 558/80
See application file for complete search history.

(56) References Cited

U.S. PATENT DOCUMENTS 6,080,826 A * 6/2000 Grubbs et al. ............... 526/75
6,111,121 A * 8/2000 Grubbs et al. ............... 556/21

OTHER PUBLICATIONS

"DuPont™ Tyzor® Organic Titanates, Technical Note—Polyesterification Catalyst," DuPont technical data sheet (2001).
"DuPont™ TYZOR® Organic Titanates, Technical Note—Transesterification," DuPont technical data sheet (2001).
Bourissou et al. (2000), "Stable Carbenes," *Chemical Reviews* 100(1):39-91.
Mancini et al. (1999), "Recyclability of Pet from Virgin Resin," *Materials Research* 2(1):33-38.
Nadkarni (1999), "Polyester Waste Recycling: Sources, Processing Methods and End Uses," *International Fiber Journal* 14(3), printed from http://www.fiberjournal.com/issue/june99/polyester.html.
Nyce et al. (2002), "Expanding the Catalytic Activity of Nucleophilic N-Heterocyclic Carbenes for Transesterification Reactions," *Organic Letters* 4(21):3587-3590.
Sako et al. (1997), "Depolymerization of Polyethylene Terephthalate to Monomers with Supercritical Methanol," *Proc. of the 4th International Symposium on Supercritical Fluids*, pp. 107-110 (abstract only).

* cited by examiner

*Primary Examiner*—Kamal A. Saeed
(74) *Attorney, Agent, or Firm*—Reed Intellectual Property Law Group

(57) ABSTRACT

A method is provided for carrying out depolymerization of a polymer containing electrophilic linkages in the presence of a catalyst and a nucleophilic reagent, wherein production of undesirable byproducts resulting from polymer degradation is minimized. The reaction can be carried out at a temperature of 80° C. or less, and generally involves the use of an organic, nonmetallic catalyst, thereby ensuring that the depolymerization product(s) are substantially free of metal contaminants. In an exemplary depolymerization method, the catalyst is a carbene compound such as an N-heterocyclic carbene, or is a precursor to a carbene compound. The method provides an important alternative to current recycling techniques such as those used in the degradation of polyesters, polyamides, and the like.

26 Claims, 2 Drawing Sheets

HETEROATOM-STABILIZED CARBENES AND PRECURSORS THERETO AS DEPOLYMERIZATION CATALYSTS

CROSS-REFERENCE TO RELATED APPLICATIONS

This is a divisional of U.S. patent application Ser. No. 10/330,853 filed Dec. 26, 2002, now U.S. Pat. No. 6,911,546 the disclosure of which is incorporated by reference in its entirety.

ACKNOWLEDGEMENT OF GOVERNMENT SUPPORT

This invention was made in part with Government support under a grant from the National Science Foundation (Cooperative Agreement No. DMR-980677). Accordingly, the Government may have certain rights to this invention.

TECHNICAL FIELD

This invention relates generally to the depolymerization of polymers, and, more particularly relates to an organocatalytic method for depolymerizing polymers using nucleophilic reagents. The invention is applicable in numerous fields, including industrial chemistry and chemical waste disposal, plastics recycling, and manufacturing processes requiring a simple and convenient method for the degradation of polymers.

BACKGROUND OF THE INVENTION

Technological advances of all kinds continue to present many complex ecological issues. Consequently, waste management and pollution prevention are two very significant challenges of the $21^{st}$ century. The overwhelming quantity of plastic refuse has significantly contributed to the critical shortage of landfill space faced by many communities. For example, poly(ethylene terephthalate) (poly(oxy-1,2-ethanediyl-oxycarbonyl-1,4-diphenylenecarbonyl); "PET"), a widely used engineering thermoplastic for carpeting, clothing, tire cords, soda bottles and other containers, film, automotive applications, electronics, displays, etc. will contribute more than 1 billion pounds of waste to land-fills in 2002 alone. The worldwide production of PET has been growing at an annual rate of 10% per year, and with the increase in use in electronic and automotive applications, this rate is expected to increase significantly to 15% per year. Interestingly, the precursor monomers represent only about 2% of the petrochemical stream. Moreover, the proliferation of the use of organic solvents, halogenated solvents, water, and energy consumption in addressing the need to recycle commodity polymers such as PET and other polyesters has created the need for environmentally responsible and energy efficient recycling processes. See Nadkarni (1999) *International Fiber Journal* 14 (3).

Significant effort has been invested in researching recycling strategies for PET, and these efforts have produced three commercial options; mechanical, chemical and energy recycling. Energy recycling simply burns the plastic for its calorific content. Mechanical recycling, the most widespread approach, involves grinding the polymer to powder, which is then mixed with "virgin" PET. See Mancini et al. (1999) *Materials Research* 2 (1):33–38. Many chemical companies use this process in order to recycle PET at the rate of approximately 50,000 tons/year per plant. In Europe, all new packaging materials as of 2002 must contain 15% recycled material. However, it has been demonstrated that successive recycling steps cause significant polymer degradation, in turn resulting in a loss of desirable mechanical properties. Recycling using chemical degradation involves a process that depolymerizes a polymer to starting material, or at least to relative short oligomeric components. Clearly, this process is most desirable, but is the most difficult to control since elevated temperature and pressure are required along with a catalyst composed of a strong base, or an organometallic complex such as an organic titanate. See Sako et al. (1997) *Proc. of the $4^{th}$ Int'l Symposium on Supercritical Fluids*, pp. 107–110. The use of such a catalyst results in significant quantities of undesirable byproducts, and materials processed by these methods are thus generally unsuitable for use in medical materials or food packaging, limiting their utility. Moreover, the energy required to effect depolymerization essentially eliminates sustainability arguments.

Accordingly, there is a need in the art for an improved depolymerization method. Ideally, such a method would not involve extreme reaction conditions, use of metallic catalysts, or a process that results in significant quantities of potentially problematic by-products.

SUMMARY OF THE INVENTION

The invention is directed to the aforementioned need in the art, and, as such, provides an efficient catalytic depolymerization reaction that employs mild conditions, wherein production of undesirable byproducts resulting from polymer degradation is minimized. The reaction can be carried out at temperatures of at most 80° C., and, because a nonmetallic catalyst is preferably employed, the depolymerization products, in a preferred embodiment, are substantially free of metal contaminants. With many of the carbene catalysts disclosed herein, the depolymerization reaction can be carried out at a temperature of at most 60° C. or even 30° C. or lower, i.e., at room temperature.

More specifically, in one aspect of the invention, a method is provided for depolymerizing a polymer having a backbone containing electrophilic linkages, wherein the method involves contacting the polymer with a nucleophilic reagent and a catalyst at a temperature of less than 80° C. An important application of this method is in the depolymerization of polyesters, including homopolymeric polyesters (in which all of the electrophilic linkages are ester linkages) and polyester copolymers (in which a fraction of the electrophilic linkages are ester linkages and the remainder of the electrophilic linkages are other than ester linkages).

In a related aspect of the invention, a method is provided for depolymerizing a polymer having a backbone containing electrophilic linkages, wherein the method involves contacting the polymer with a nucleophilic reagent and a catalyst that yields depolymerization products that are substantially free of metal contaminants. The polymer may be, for example, a polyester, a polycarbonate, a polyurethane, or a related polymer, in either homopolymeric or copolymeric form, as indicated above. In this embodiment, in order to provide reaction products that are substantially free of contamination by metals and metal-containing compounds, the catalyst used is a purely organic, nonmetallic catalyst. Preferred catalysts herein are carbene compounds, which act as nucleophilic catalysts, as well as precursors to carbene compounds, as will be discussed infra. As is well understood in the art, carbenes are electronically neutral compounds containing a divalent carbon atom with only six electrons in its valence shell. Carbenes include, by way of example, cyclic diaminocarbenes, imidazol-2-ylidenes (e.g., 1,3-dimesityl-imidazol-2-ylidene and 1,3-dimesityl-4,5-dihydroimidazol-2-ylidene), 1,2,4-triazol-3-ylidenes, and 1,3-thiazol-2-ylidenes; see Bourissou et al. (2000) *Chem. Rev.* 100:39–91.

Since the initial description of the synthesis, isolation, and characterization of stable carbenes by Arduengo (Arduengo et al. (1991) *J. Am. Chem. Soc.* 113:361; Arduengo et al. (1992) *J. Am. Chem. Soc.* 114:5530), the exploration of their chemical reactivity has become a major area of research. See, e.g., Arduengo et al. (1999) *Acc. Chem. Res.* 32:913; Bourissou et al. (2000), supra; and Brode (1995) *Angew. Chem. Int. Ed. Eng.* 34:1021. Although carbenes have now been extensively investigated, and have in fact been established as useful in many synthetically important reactions, there has been no disclosure or suggestion to use carbenes as catalysts in nucleophilic depolymerization reactions, i.e., reactions in which a polymer containing electrophilic linkages is depolymerized with a nucleophilic reagent in the presence of a carbene catalyst.

Suitable catalysts for use herein thus include heteroatom-stabilized carbenes or precursors to such carbenes. The heteroatom-stabilized carbenes have the structure of formula (I)

wherein:

$E^1$ and $E^2$ are independently selected from N, $NR^E$, O, P, $PR^E$, and S, $R^E$ is hydrogen, heteroalkyl, or heteroaryl, x and y are independently zero, 1, or 2, and are selected to correspond to the valence state of $E^1$ and $E^2$, respectively, and wherein when $E^1$ and $E^2$ are other than O or S, then $E^1$ and $E^2$ may be linked through a linking moiety that provides a heterocyclic ring in which $E^1$ and $E^2$ are incorporated as heteroatoms;

$R^1$ and $R^2$ are independently selected from branched $C_3$–$C_{30}$ hydrocarbyl, substituted branched $C_3$–$C_{30}$ hydrocarbyl, heteroatom-containing branched $C_4$–$C_{30}$ hydrocarbyl, substituted heteroatom-containing branched $C_4$–$C_{30}$ hydrocarbyl, cyclic $C_5$–$C_{30}$ hydrocarbyl, substituted cyclic $C_5$–$C_{30}$ hydrocarbyl, heteroatom-containing cyclic $C_1$–$C_{30}$ hydrocarbyl, and substituted heteroatom-containing cyclic $C_1$–$C_{30}$ hydrocarbyl;

$L^1$ and $L^2$ are linkers containing 1 to 6 spacer atoms, and are independently selected from heteroatoms, substituted heteroatoms, hydrocarbylene, substituted hydrocarbylene, heteroatom-containing hydrocarbylene, and substituted heteroatom-containing hydrocarbylene; and m and n are independently zero or 1, such that $L^1$ and $L^2$ are optional.

Certain carbene catalysts of formula (I) are novel chemical compounds and are claimed as such herein. These novel carbenes are those wherein a heteroatom is directly bound to $E^1$ and/or $E^2$, and include, solely by way of example, carbenes of formula (I) wherein $E^1$ is $NR^E$ and $R^E$ is a heteroalkyl or heteroaryl group such as an alkoxy, alkylthio, aryloxy, arylthio, aralkoxy, or aralkylthio moiety.

Carbene precursors suitable as catalysts herein include tri-substituted methanes having the structure of formula (PI), metal adducts having the structure of formula (PII), and tetrasubstituted olefins having the structure (PIII)

wherein, in formulae (PI) and (PII):

$E^1$ and $E^2$ are independently selected from N, $NR^E$, O, P, $PR^E$, and S, $R^E$ is hydrogen, heteroalkyl, or heteroaryl, x and y are independently zero, 1, or 2, and are selected to correspond to the valence state of $E^1$ and $E^2$, respectively, and wherein when $E^1$ and $E^2$ are other than O or S, then $E^1$ and $E^2$ may be linked through a linking moiety that provides a heterocyclic ring in which $E^1$ and $E^2$ are incorporated as heteroatoms;

$R^1$ and $R^2$ are independently selected from branched $C_3$–$C_{30}$ hydrocarbyl, substituted branched $C_3$–$C_{30}$ hydrocarbyl, heteroatom-containing branched $C_4$–$C_{30}$ hydrocarbyl, substituted heteroatom-containing branched $C_4$–$C_{30}$ hydrocarbyl, cyclic $C_5$–$C_{30}$ hydrocarbyl, substituted cyclic $C_5$–$C_{30}$ hydrocarbyl, heteroatom-containing cyclic $C_1$–$C_{30}$ hydrocarbyl, and substituted heteroatom-containing cyclic $C_1$–$C_{30}$ hydrocarbyl;

$L^1$ and $L^2$ are linkers containing 1 to 6 spacer atoms, and are independently selected from heteroatoms, substituted heteroatoms, hydrocarbylene, substituted hydrocarbylene, heteroatom-containing hydrocarbylene, and substituted heteroatom-containing hydrocarbylene;

m and n are independently zero or 1;

$R^7$ is selected from alkyl, heteroalkyl, aryl, heteroaryl, aralkyl, or heteroaralkyl, substituted with at least one electron-withdrawing substituent;

M is a metal;

Ln is a ligand; and j is the number of ligands bound to M.

In compounds of formula (PIII), the substituents are as follows:

$E^3$ and $E^4$ are defined as for $E^1$ and $E^2$;

v and w are defined as for x and y;

$R^8$ and $R^9$ are defined as for $R^1$ and $R^2$;

$L^3$ and $L^4$ are defined as for $L^1$ and $L^2$; and h and k are defined as for m and n.

The carbene precursors may be in the form of a salt, in which case the precursor is positively charged and associated with an anionic counterion, such as a halide ion (I, Br, Cl), a hexafluorophosphate anion, or the like.

Novel carbene precursors herein include compounds of formula (PI), those compounds of formula (PII) in which a heteroatom is directly bound to $E^1$ and/or $E^2$, and those compounds of formula (PIII) in which a heteroatom is directly bound to at least one of $E^1$, $E^2$, $E^3$, and $E^4$, and may be in the form of a salt as noted above.

Ideally, the carbene catalyst used in conjunction with the present depolymerization reaction is an N-heterocyclic carbene having the structure of formula (II)

(II)

wherein:

R¹, R², L¹, L², m, and n are as defined above; and

L is a hydrocarbylene, substituted hydrocarbylene, heteroatom-containing hydrocarbylene, or substituted heteroatom-containing hydrocarbylene linker, wherein two or more substituents on adjacent atoms within L may be linked to form an additional cyclic group.

As alluded to above, one important application of the present invention is in the recycling of polyesters, including, by way of illustration and not limitation: PET; poly (butylene terephthalate) (PBT); poly(alkylene adipate)s and their copolymers; and poly(ε-caprolactone). The methodology of the invention provides an efficient means to degrade such polymers into their component monomers and/or relatively short oligomeric fragments without need for extreme reaction conditions or metallic catalysts.

DETAILED DESCRIPTION OF THE INVENTION

Unless otherwise indicated, this invention is not limited to specific polymers, carbene catalysts, nucleophilic reagents, or depolymerization conditions. The terminology used herein is for the purpose of describing particular embodiments only and is not intended to be limiting.

As used in the specification and the appended claims, the singular forms "a," "an," and "the" include plural referents unless the context clearly dictates otherwise. Thus, for example, reference to "a polymer" encompasses a combination or mixture of different polymers as well as a single polymer, reference to "a catalyst" encompasses both a single catalyst as well as two or more catalysts used in combination, and the like.

In this specification and in the claims that follow, reference will be made to a number of terms, which shall be defined to have the following meanings:

As used herein, the phrase "having the formula" or "having the structure" is not intended to be limiting and is used in the same way that the term "comprising" is commonly used.

The term "alkyl" as used herein refers to a linear, branched, or cyclic saturated hydrocarbon group typically although not necessarily containing 1 to about 20 carbon atoms, preferably 1 to about 12 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl and the like. Generally, although again not necessarily, alkyl groups herein contain 1 to about 12 carbon atoms. The term "lower alkyl" intends an alkyl group of 1 to 6 carbon atoms, and the specific term "cycloalkyl" intends a cyclic alkyl group, typically having 4 to 8, preferably 5 to 7, carbon atoms. The term "substituted alkyl" refers to alkyl substituted with one or more substituent groups, and the terms "heteroatom-containing alkyl" and "heteroalkyl" refer to alkyl in which at least one carbon atom is replaced with a heteroatom. If not otherwise indicated, the terms "alkyl" and "lower alkyl" include linear, branched, cyclic, unsubstituted, substituted, and/or heteroatom-containing alkyl and lower alkyl, respectively.

The term "alkylene" as used herein refers to a difunctional linear, branched, or cyclic alkyl group, where "alkyl" is as defined above.

The term "alkenyl" as used herein refers to a linear, branched, or cyclic hydrocarbon group of 2 to about 20 carbon atoms containing at least one double bond, such as ethenyl, n-propenyl, isopropenyl, n-butenyl, isobutenyl, octenyl, decenyl, tetradecenyl, hexadecenyl, cicosenyl, tetracosenyl, and the like. Preferred alkenyl groups herein contain 2 to about 12 carbon atoms. The term "lower alkenyl" intends an alkenyl group of 2 to 6 carbon atoms, and the specific term "cycloalkenyl" intends a cyclic alkenyl group, preferably having 5 to 8 carbon atoms. The term "substituted alkenyl" refers to alkenyl substituted with one or more substituent groups, and the terms "heteroatom-containing alkenyl" and "heteroalkenyl" refer to alkenyl in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl, respectively.

The term "alkenylene" as used herein refers to a difunctional linear, branched, or cyclic alkenyl group, where "alkenyl" is as defined above.

The term "alkoxy" as used herein refers to a group —O-alkyl wherein "alkyl" is as defined above, and the term "alkylthio" as used herein refers to a group —S-alkyl wherein "alkyl is as defined above.

The term "aryl" as used herein, and unless otherwise specified, refers to an aromatic substituent containing a single aromatic ring or multiple aromatic rings that are fused together, directly linked, or indirectly linked (such that the different aromatic rings are bound to a common group such as a methylene or ethylene moiety). Preferred aryl groups contain 5 to 20 carbon atoms and either one aromatic ring or 2 to 4 fused or linked aromatic rings, e.g., phenyl, naphthyl, biphenyl, and the like, with more preferred aryl groups containing 1 to 3 aromatic rings, and particularly preferred aryl groups containing 1 or 2 aromatic rings and 5 to 14 carbon atoms. "Substituted aryl" refers to an aryl moiety substituted with one or more substituent groups, and the terms "heteroatom-containing aryl" and "heteroaryl" refer to aryl in which at least one carbon atom is replaced with a heteroatom. Unless otherwise indicated, the terms "aromatic," "aryl," and "arylene" include heteroaromatic, substituted aromatic, and substituted heteroaromatic species.

The term "aryloxy" refers to a group —O-aryl wherein "aryl" is as defined above.

The term "alkaryl" refers to an aryl group with at least one and typically 1 to 6 alkyl, preferably 1 to 3, alkyl substituents, and the term "aralkyl" refers to an alkyl group with an aryl substituent, wherein "aryl" and "alkyl" are as defined above. Alkaryl groups include, for example, p-methylphenyl, 2,4-dimethylphenyl, 2,4,6-trimethylphenyl, and the like. The term "aralkyl" refers to an alkyl group substituted with an aryl moiety, wherein "alkyl" and "aryl" are as defined above.

The term "alkaryloxy" refers to a group —O—R wherein R is alkaryl, the term "alkarylthio" refers to a group —S—R wherein R is alkaryl, the term aralkoxy refers to a group —O—R wherein R is aralkyl, the term "aralkylthio" refers to a group —S—R wherein R is aralkyl.

The terms "halo," "halide," and "halogen" are used in the conventional sense to refer to a chloro, bromo, fluoro, or iodo substituent. The terms "haloalkyl," "haloalkenyl," and "haloalkynyl" (or "halogenated alkyl," "halogenated alkenyl," and "halogenated alkynyl") refer to an alkyl, alkenyl, or alkynyl group, respectively, in which at least one of the hydrogen atoms in the group has been replaced with a halogen atom.

"Hydrocarbyl" refers to univalent hydrocarbyl radicals containing 1 to about 30 carbon atoms, preferably 1 to about 20 carbon atoms, more preferably 1 to about 12 carbon atoms, including linear, branched, cyclic, saturated, and unsaturated species, such as alkyl groups, alkenyl groups, aryl groups, alkaryl groups, and the like. The term "lower hydrocarbyl" intends a hydrocarbyl group of 1 to 6 carbon atoms, and the term "hydrocarbylene" intends a divalent hydrocarbyl moiety containing 1 to about 30 carbon atoms, preferably 1 to about 20 carbon atoms, most preferably 1 to about 12 carbon atoms, including linear, branched, cyclic, saturated and unsaturated species. The term "lower hydrocarbylene" intends a hydrocarbylene group of 1 to 6 carbon atoms. Unless otherwise indicated, the terms "hydrocarbyl" and "hydrocarbylene" are to be interpreted as including substituted and/or heteroatom-containing hydrocarbyl and hydrocarbylene moieties, respectively.

The term "heteroatom-containing" as in a "heteroatom-containing alkyl group" (also termed a "heteroalkyl" group) or a "heteroatom-containing aryl group" (also termed a "heteroaryl" group) refers to a molecule, linkage, or substituent in which one or more carbon atoms are replaced with an atom other than carbon, e.g., nitrogen, oxygen, sulfur, phosphorus or silicon, typically nitrogen, oxygen or sulfur. Similarly, the term "heteroalkyl" refers to an alkyl substituent that is heteroatom-containing, the term "heterocyclic" refers to a cyclic substituent that is heteroatom-containing, the terms "heteroaryl" and heteroaromatic" respectively refer to "aryl" and "aromatic" substituents that are heteroatom-containing, and the like. Examples of heteroalkyl groups include alkoxyaryl, alkylsulfanyl-substituted alkyl, N-alkylated amino alkyl, and the like. Examples of heteroaryl substituents include pyrrolyl, pyrrolidinyl, pyridinyl, quinolinyl, indolyl, pyrimidinyl, imidazolyl, 1,2,4-triazolyl, tetrazolyl, etc., and examples of heteroatom-containing alicyclic groups are pyrrolidino, morpholino, piperazino, piperidino, etc. It should be noted that a "heterocyclic" group or compound may or may not be aromatic, and further that "heterocycles" may be monocyclic, bicyclic, or polycyclic as described above with respect to the term "aryl."

By "substituted" as in "substituted hydrocarbyl," "substituted alkyl," "substituted aryl," and the like, as alluded to in some of the aforementioned definitions, is meant that in the hydrocarbyl, alkyl, aryl, or other moiety, at least one hydrogen atom bound to a carbon (or other) atom is replaced with a non-hydrogen substituent. Examples of such substituents include, without limitation, functional groups such as halide, hydroxyl, sulfhydryl, $C_1$–$C_{20}$ alkoxy, $C_5$–$C_{20}$ aryloxy, $C_2$–$C_{20}$ acyl (including $C_2$–$C_{20}$ alkylcarbonyl (—CO-alkyl) and $C_6$–$C_{20}$ arylcarbonyl (—CO-aryl)), acyloxy (—O-acyl), $C_2$–$C_{20}$ alkoxycarbonyl (—(CO)—O-alkyl), $C_6$–$C_{20}$ aryloxycarbonyl (—(CO)—O-aryl), halocarbonyl (—CO)—X where X is halo), $C_2$–$C_{20}$ alkyl-carbonato (—O—(CO)—O-alkyl), $C_6$–$C_{20}$ arylcarbonato (—O—(CO)—O-aryl), carboxy (—COOH), carboxylato (—COO$^-$), carbamoyl (—(CO)—NH$_2$), mono-($C_1$–$C_{20}$ alkyl)-substituted carbamoyl (—(CO)—NH($C_1$–$C_{20}$ alkyl)), di-($C_1$–$C_{20}$ alkyl)-substituted carbamoyl —(CO)—N($C_1$–$C_{20}$ alkyl)$_2$), mono-substituted arylcarbamoyl (—(CO)—NH-aryl), thiocarbamoyl (—(CS)—NH$_2$), carbamido (—NH—(CO)—NH$_2$), cyano (—C≡N), cyanato (—O—C≡N), formyl (—(CO)—H), thioformyl (—(CS)—H), amino (—NH$_2$), mono- and di-($C_1$–$C_{20}$ alkyl)-substituted amino, mono- and di-($C_5$–$C_{20}$ aryl)-substituted amino, $C_2$–$C_{20}$ alkylamido (—NH—(CO)-alkyl), $C_6$–$C_{20}$ arylamido (—NH—(CO)-aryl), imino (—CR=NH where R=hydrogen, $C_1$–$C_{20}$ alkyl, $C_5$–$C_{20}$ aryl, $C_6$–$C_{24}$ alkaryl, $C_6$–$C_{24}$ aralkyl, etc.), alkylimino (—CR=N(alkyl), where R=hydrogen, alkyl, aryl, alkaryl, etc.), arylimino (—CR=N(aryl), where R=hydrogen, alkyl, aryl, alkaryl, etc.), nitro (—NO$_2$), nitroso (—NO), sulfo (—SO$_2$—OH), sulfonato (—SO$_2$—O$^-$), $C_1$–$C_{20}$ alkylsulfanyl (—S-alkyl; also termed "alkylthio"), arylsulfanyl (—S-aryl; also termed "arylthio"), $C_1$–$C_{20}$ alkylsulfinyl (—(SO)-alkyl), $C_5$–$C_{20}$ arylsulfinyl (—(SO)-aryl), $C_1$–$C_{20}$ alkylsulfonyl (—SO$_2$-alkyl), $C_5$–$C_{20}$ arylsulfonyl (—SO$_2$-aryl), and thiocarbonyl (=S); and the hydrocarbyl moieties $C_1$–$C_{20}$ alkyl (preferably $C_1$–$C_{18}$ alkyl, more preferably $C_1$–$C_{12}$ alkyl, most preferably $C_1$–$C_6$ alkyl), $C_2$–$C_{20}$ alkenyl (preferably $C_2$–$C_{18}$ alkenyl, more preferably $C_2$–$C_{12}$ alkenyl, most preferably $C_2$–$C_6$ alkenyl), $C_2$–$C_{20}$ alkynyl (preferably $C_2$–$C_{18}$ alkynyl, more preferably $C_2$–$C_{12}$ alkynyl, most preferably $C_2$–$C_6$ alkynyl), $C_5$–$C_{20}$ aryl (preferably $C_5$–$C_{14}$ aryl), $C_6$–$C_{24}$ alkaryl (preferably $C_6$–$C_{18}$ alkaryl), and $C_6$–$C_{24}$ aralkyl (preferably $C_6$–$C_{18}$ aralkyl).

In addition, the aforementioned functional groups may, if a particular group permits, be further substituted with one or more additional functional groups or with one or more hydrocarbyl moieties such as those specifically enumerated above. Analogously, the above-mentioned hydrocarbyl moieties may be further substituted with one or more functional groups or additional hydrocarbyl moieties such as those specifically enumerated.

By "substantially free of" a particular type of chemical compound is meant that a composition or product contains less 10 wt. % of that chemical compound, preferably less than 5 wt. %, more preferably less than 1 wt. %, and most preferably less than 0.1 wt. %. For instance, the depolymerization product herein is "substantially free of" metal contaminants, including metals per se, metal salts, metallic complexes, metal alloys, and organometallic compounds.

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

Accordingly, the invention features a method for depolymerizing a polymer having a backbone containing electrophilic linkages. The electrophilic linkages may be, for example, ester linkages (—(CO)—O—), carbonate linkages (—O—(CO)—O—), urethane linkages (—O—(CO)—NH), substituted urethane linkages (—O—(CO)—NR—, where R is a nonhydrogen substituent such as alkyl, aryl, alkaryl, or the like), amido linkages (—(CO)—NH—), substituted amido linkages (—(CO)—NR— where R is as defined previously, thioester linkages (—(CO)—S—), sulfonic ester linkages (—S(O)$_2$—O—), and the like. Other electrophilic linkages that can be cleaved using nucleophilic reagents will be known to those of ordinary skill in the art of organic chemistry and polymer science and/or can be readily found by reference to the pertinent texts and literature. The polymer undergoing depolymerization may be linear or branched, and may be a homopolymer or copolymer, the latter including random, block, multiblock, and alternating copolymers, terpolymers, and the like. Examples of polymers that can be depolymerized using the methodology of the invention include, without limitation:

poly(alkylene terephthalates) such as fiber-grade PET (a homopolymer made from monoethylene glycol and terephthalic acid), bottle-grade PET (a copolymer made based on monoethylene glycol, terephthalic acid, and other comonomers such as isophthalic acid, cyclohexene dimethanol, etc.), poly (butylene terephthalate) (PBT), and poly(hexamethylene terephthalate);

poly(alkylene adipates) such as poly(ethylene adipate), poly(1,4-butylene adipate), and poly(hexamethylene adipate);

poly(alkylene suberates) such as poly(ethylene suberate);

poly(alkylene sebacates) such as poly(ethylene sebacate);

poly(ε-caprolactone) and poly(β-propiolactone);

poly(alkylene isophthalates) such as poly(ethylene isophthalate);

poly(alkylene 2,6-naphthalene-dicarboxylates) such as poly(ethylene 2,6-naphthalene-dicarboxylate);

poly(alkylene sulfonyl-4,4'-dibenzoates) such as poly(ethylene sulfonyl-4,4'-dibenzoate);

poly(p-phenylene alkylene dicarboxylates) such as poly(p-phenylene ethylene dicarboxylates);

poly(trans-1,4-cyclohexanediyl alkylene dicarboxylates) such as poly(trans-1,4-cyclohexanediyl ethylene dicarboxylate);

poly(1,4-cyclohexane-dimethylene alkylene dicarboxylates) such as poly(1,4-cyclohexane-dimethylene ethylene dicarboxylate);

poly([2.2.2]-bicyclooctane-1,4-dimethylene alkylene dicarboxylates) such as poly([2.2.2]-bicyclooctane-1,4-dimethylene ethylene dicarboxylate);

lactic acid polymers and copolymers such as (S)-polylactide, (R,S)-polylactide, poly(tetramethylglycolide), and poly(lactide-co-glycolide); and polycarbonates of bisphenol A, 3,3'-dimethylbisphenol A, 3,3',5,5'-tetrachlorobisphenol A, 3,3',5,5'-tetramethylbisphenol A;

polyamides such as poly(p-phenylene terephthalamide) (Kevlar®);

poly(alkylene carbonates) such as poly(propylene carbonate);

polyurethanes such as those available under the tradenames Baytece® and Bayfil®, from Bayer Corporation; and polyurethane/polyester copolymers such as that available under the tradename Bayda®, from Bayer Corporation.

Depolymerization of the polymer is carried out, as indicated above, in the presence of a nucleophilic reagent and a catalyst. Nucleophilic reagents, as will be appreciated by those of ordinary skill in the art, include monohydric alcohols, diols, polyols, thiols, primary amines, and the like, and may contain a single nucleophilic moiety or two or more nucleophilic moieties, e.g., hydroxyl, sulfhydryl, and/or amino groups. The nucleophilic reagent is selected to correspond to the particular electrophilic linkages in the polymer backbone, such that nucleophilic attack at the electrophilic linkage results in cleavage of the linkage. For example, a polyester can be cleaved at the ester linkages within the polymer backbone using an alcohol, preferably a primary alcohol, most preferably a $C_2$–$C_4$ monohydric alcohol such as ethanol, isopropanol, and t-butyl alcohol. It will be appreciated that such a reaction cleaves the ester linkages via a transesterification reaction, as will be illustrated infra.

The preferred catalysts for the depolymerization reaction are carbenes and carbene precursors. Carbenes include, for instance, diarylcarbenes, cyclic diaminocarbenes, imidazol-2-ylidenes, 1,2,4-triazol-3-ylidenes, 1,3-thiazol-2-ylidenes, acyclic diaminocarbenes, acyclic aminooxycarbenes, acyclic aminothiocarbenes, cyclic diborylcarbenes, acyclic diborylcarbenes, phosphinosilylcarbenes, phosphinophosphoniocarbenes, sulfenyl-trifluoromethylcarbene, and sulfenyl-pentafluorothiocarbene. See Bourissou et al. (2000), cited supra. Preferred carbenes are heteroatom-stabilized carbenes and preferred carbene precursors are precursors to heteroatom-stabilized carbenes. nitrogen-containing carbenes, with N-heterocyclic carbenes most preferred.

In one embodiment, heteroatom-stabilized carbenes suitable as depolymerization catalysts herein have the structure of formula (I)

(I)

wherein the various substituents are as follows:

$E^1$ and $E^2$ are independently selected from N, $NR^E$, O, P, $PR^E$, and S, $R^E$ is hydrogen, heteroalkyl, or heteroaryl, and x and y are independently zero, 1, or 2, and are selected to correspond to the valence state of $E^1$ and $E^2$, respectively. When $E^1$ and $E^2$ are other than O or S, then $E^1$ and $E^2$ may be linked through a linking moiety that provides a heterocyclic ring in which $E^1$ and $E^2$ are incorporated as heteroatoms. In the latter case, the heterocyclic ring may be aliphatic or aromatic, and may contain substituents and/or heteroatoms. Generally, such a cyclic group will contain 5 or 6 ring atoms.

For example, in representative compounds of formula (I):

(1) $E^1$ is O or S and x is 1;
(2) $E^1$ is N, x is 1, and $E^1$ is linked to $E^2$;
(3) $E^1$ is N, x is 2, and $E^1$ and $E^2$ are not linked;
(4) $E^1$ is $NR^E$, x is 1, and $E^1$ and $E^2$ are not linked; or
(5) $E^1$ is $NR^E$, x is zero, and $E^1$ is linked to $E^2$.

$R^1$ and $R^2$ are independently selected from branched $C_3$–$C_{30}$ hydrocarbyl, substituted branched $C_3$–$C_{30}$ hydrocarbyl, heteroatom-containing branched $C_4$–$C_{30}$ hydrocarbyl, substituted heteroatom-containing branched $C_4$–$C_{30}$ hydrocarbyl, cyclic $C_5$–$C_{30}$ hydrocarbyl, substituted cyclic $C_5$–$C_{30}$ hydrocarbyl, heteroatom-containing cyclic $C_1$–$C_{30}$ hydrocarbyl, and substituted heteroatom-containing cyclic $C_1$–$C_{30}$ hydrocarbyl. Preferably, at least one of $R^1$ and $R^2$, and more preferably both $R^1$ and $R^2$, are relatively bulky groups, particularly branched alkyl (including substituted and/or heteroatom-containing alkyl), aryl (including substituted aryl, heteroaryl, and substituted heteroaryl), alkaryl (including substituted and/or heteroatom-containing aralkyl), and alicyclic. Using such sterically bulky groups to protect the highly reactive carbene center has been found to kinetically stabilize singlet carbenes, which are preferred reaction catalysts herein. Particular sterically bulky groups that are suitable as $R^1$ and $R^2$ are optionally substituted and/or heteroatom-containing $C_3$–$C_{12}$ alkyl, tertiary $C_4$–$C_{12}$ alkyl, $C_5$–$C_{12}$ aryl, $C_6$–$C_{18}$ alkaryl, and $C_5$–$C_{12}$ alicyclic, with $C_5$–$C_{12}$ aryl and $C_6$–$C_{12}$ alkaryl particularly preferred. The latter substituents are exemplified by phenyl optionally substituted with 1 to 3 substituents selected from lower alkyl, lower alkoxy, and halogen, and thus include, for example, p-methylphenyl, 2,6-dimethylphenyl, and 2,4,6-trimethylphenyl (mesityl).

$L^1$ and $L^2$ are linkers containing 1 to 6 spacer atoms, and are independently selected from heteroatoms, substituted heteroatoms, hydrocarbylene, substituted hydrocarbylene, heteroatom-containing hydrocarbylene, and substituted heteroatom-containing hydrocarbylene; and m and n are independently zero or 1, meaning that each of $L^1$ and $L^2$ is optional. Preferred $L^1$ and $L^2$ moieties include, by way of example, alkylene, alkenylene, arylene, aralkylene, any of which may be heteroatom-containing and/or substituted, or $L^1$ and/or $L^2$ may be a heteroatom such as O or S, or a substituted heteroatom such as NH, NR (where R is alkyl, aryl, other hydrocarbyl, etc.), or PR; and

In one preferred embodiment, $E^1$ and $E^2$ are independently N or $NR^E$ and are not linked, such that the carbene is an N-heteroacyclic carbene. In another preferred embodiment, $E^1$ and $E^2$ are N, x and y are 1, and $E^1$ and $E^2$ are linked through a linking moiety such that the carbene is an N-heterocyclic carbene. N-heterocyclic carbenes suitable herein include, without limitation, compounds having the structure of formula (II)

(II)

wherein $R^1$, $R^2$, $L^1$, $L^2$, m, and n are as defined above for carbenes of formula (I). In carbenes of structural formula (II), L is a hydrocarbylene, substituted hydrocarbylene, heteroatom-containing hydrocarbylene, or substituted heteroatom-containing hydrocarbylene linker, wherein two or more substituents on adjacent atoms within L may be linked to form an additional cyclic group. L is a hydrocarbylene, substituted hydrocarbylene, heteroatom-containing hydrocarbylene, or substituted heteroatom-containing hydrocarbylene linker, wherein two or more substituents on adjacent atoms within L may be linked to form an additional cyclic group. For example, L may be —$CR^3R^4$—$CR^5R^6$— or —$CR^3$=$CR^5$—, wherein $R^3$, $R^4$, $R^5$, and $R^6$ are independently selected from hydrogen, halogen, $C_1$–$C_{12}$ alkyl, or wherein any two of $R^3$, $R^4$, $R^5$, and $R^6$ may be linked together to form a substituted or unsubstituted, saturated or unsaturated ring.

Accordingly, when L is —$CR^3R^4$—$CR^5R^6$— or —$CR^3$=$CR^5$—, the carbene has the structure of formula (III)

(III)

in which q is an optional double bond, s is zero or 1, and t is zero or 1, with the proviso that when q is present, s and t are zero, and when q is absent, s and t are 1.

Certain carbenes are new chemical compounds and are claimed as such herein. These are compounds having the structure of formula (I) wherein a heteroatom is directly bound to $E^1$ and/or $E^2$. These novel carbenes are those wherein a heteroatom is directly bound to $E^1$ and/or $E^2$, and include, solely by way of example, carbenes of formula (I) wherein $E^1$ and/or $E^2$ is $NR^E$ and $R^E$ is a heteroalkyl or heteroaryl group such as an alkoxy, alkylthio, aryloxy, arylthio, aralkoxy, or aralkylthio moiety. Other such carbenes are those wherein x and/or y is at least 1, and $L^1$ and/or $L^2$ is heteroalkyl, heteroaryl, or the like, wherein the heteroatom within $L^1$ and/or $L^2$ is directly bound to $E^1$ and/or $E^2$, respectively.

Representative of such novel carbenes are compounds of formula (I) wherein $E^1$ is $NR^E$, and $R^E$ is alkoxy, substituted alkoxy, aryloxy, substituted aryloxy, aralkoxy, or substituted aralkoxy. A preferred subset of such carbenes are those wherein $E^2$ is N, x is zero, y is 1, and $E^1$ and $E^2$ are linked through a substituted or unsubstituted lower alkylene or lower alkenylene linkage. A more preferred subset of such carbenes are those wherein $R^E$ is lower alkoxy or monocyclic aryl-substituted lower alkoxy, $E^1$ and $E^2$ are linked through a moiety —$CR^3R^4$—$CR^5R^6$— or —$CR^3$=$CR^5$—, wherein $R^3$, $R^4$, $R^5$, and $R^6$ are independently selected from hydrogen, halogen, and $C_1$–$C_{12}$ alkyl, n is 1, $L^2$ is lower alkylene, and $R^2$ is monocyclic aryl or substituted monocyclic aryl. Examples 8–11 describe syntheses of representative compounds within this group.

As indicated previously, suitable catalysts for the present depolymerization reaction are also precursors to carbenes, preferably precursors to N-heterocyclic and N-heteroacyclic carbenes. In one embodiment, the precursor is a tri-substituted methane compound having the structure of formula (PI)

(PI)

wherein $E^1$, $E^2$, x, y, $R^1$, $R^2$, $L^1$, $L^2$, m, and n are as defined for carbenes of structural formula (I), and wherein $R^7$ is selected from alkyl, heteroalkyl, aryl, heteroaryl, aralkyl, or heteroaralkyl, and is substituted with at least one electron-withdrawing substituent such as fluoro, fluoroalkyl (including perfluoroalkyl), chloro, nitro, acytyl. It will be appreciated that the foregoing list is not exhaustive and that any electron-withdrawing group may serve as a substituent providing that the group does not cause unwanted interaction of the catalyst with other components of the depolymerization mixture or adversely affect the depolymerization reaction in any way.

Specific examples of $R^7$ groups thus include p-nitrophenyl, 2,4-dinitrobenzyl, 1,1,2,2-tetrafluoroethyl, pentafluorophenyl, and the like.

Catalysts of formula (PI) are new chemical entities. Representative syntheses of such compounds are described in Examples 13 and 14 herein. As may be deduced from those examples, compounds of formula (PI) wherein $E^1$ and $E^2$ are N may be synthesized from the corresponding diamine and an appropriately substituted aldehyde.

Another carbene precursor useful as a catalyst in the present depolymerization reaction has the structure of formula (PII)

wherein $E^1$, $E^2$, x, y, $R^1$, $R^2$, $L^1$, $L^2$, m, and n are as defined for carbenes of structural formula (I), M is a metal, e.g., gold, silver, other main group metals, or transition metals, with Ag, Cu, Ni, Co, and Fe generally preferred, and Ln is a ligand, generally an anionic or neutral ligand that may or may not be the same as $-E^1-[(L^1)_m-R^1]_x$ or $-E^2-[(L^2)_n-R^2]_y$. Generally, carbene precursors of formula (PII) can be synthesized from a carbene salt and a metal oxide; see, e.g., the synthesis described in detail in Example 12.

Still another carbene precursor suitable as a depolymerization catalyst herein is a tetrasubstituted olefin having the structure of formula (PIII)

wherein: $E^1$, $E^2$, x, y, $R^1$, $R^2$, $L^1$, $L^2$, m, and n are defined as for carbenes of structural formula (I); $E^3$ and $E^4$ are defined as for $E^1$ and $E^2$; v and w are defined as for x and y; $R^8$ and $R^9$ are defined as for $R^1$ and $R^2$; $L^3$ and $L^4$ are defined as for $L^1$ and $L^2$; and h and k are defined as for m and n. These olefins are readily formed from N,N-diaryl- and N,N-dialkyl-N-heterocyclic carbene salts and a strong base, typically an inorganic base such as a metal alkoxide.

As with the carbenes per se, those catalyst precursors having the structure of formula (PII) or (PIII) in which a heteroatom is directly bound to an "E" moiety, i.e., to $E^1$, $E^2$, $E^3$, and/or $E^4$, are new chemical entities. Preferred such precursors are those wherein the "E" moieties are $NR^E$ or linked N atoms, and the directly bound heteroatom within $R^E$ is oxygen or sulfur.

The depolymerization reaction may be carried out in an inert atmosphere by dissolving a catalytically effective amount of the selected catalyst in a solvent, combining the polymer and the catalyst solution, and then adding the nucleophilic reagent. In a particularly preferred embodiment, however, the polymer, the nucleophilic reagent, and the catalyst (e.g., a carbene or a carbene precursor) are combined and dissolved in a suitable solvent, and depolymerization thus occurs in a one-step reaction.

Preferably, the reaction mixture is agitated (e.g., stirred), and the progress of the reaction can be monitored by standard techniques, although visual inspection is generally sufficient, insofar as a transparent reaction mixture indicates that the polymer has degraded to an extent sufficient to allow all degradation products to go into solution. Examples of solvents that may be used in the polymerization reaction include organic, protic, or aqueous solvents that are inert under the depolymerization conditions, such as aromatic hydrocarbons, chlorinated hydrocarbons, ethers, aliphatic hydrocarbons, or mixtures thereof. Preferred solvents include toluene, methylene chloride, tetrahydrofuran, methyl t-butyl ether, Isopar, gasoline, and mixtures thereof. Supercritical fluids may also be used as solvents, with carbon dioxide representing one such solvent. Reaction temperatures are in the range of about 0° C. to about 100° C., typically at most 80° C., preferably 60° C. or lower, and most preferably 30° C. or less, and the reaction time will generally be in the range of about 12 to 24 hours. Pressures range from atmospheric to pressures typically used in conjunction with supercritical fluids, with the preferred pressure being atmospheric.

It is to be understood that while the invention has been described in conjunction with the preferred specific embodiments thereof, that the foregoing description as well as the examples that follow are intended to illustrate and not limit the scope of the invention. Other aspects, advantages and modifications within the scope of the invention will be apparent to those skilled in the art to which the invention pertains.

All patents, patent applications, and publications mentioned herein are hereby incorporated by reference in their entireties.

EXPERIMENTAL

General Procedures. $^1H$ and $^{13}C$ NMR spectra were recorded on a Bruke-Avance (400 MHz for $^1H$ and 100 MHz for $^{13}C$). All NMR spectra were recorded in $CDCl_3$. Materials. Solvents were obtained from Sigma-Aldrich and purified by distillation. Other reagents were obtained commercially or synthesized as follows: poly(propylene carbonate), poly(bisphenol A carbonate), poly(1,4-butylene adipate), 1-ethyl-3-methyl-1-H-imidazolium chloride, ethylene glycol, butane-2,3-dione monooxime, ammonium hexafluorophosphate, pentafluorobenzaldehyde, and mesityl diamine, obtained from Sigma-Aldrich; 1,3-(2,4,6-trimethylphenyl) imidazol-2-ylidene, synthesized according to the method of Arduengo et al. (1999) *Tetrahedron* 55:14523; N,N-diphenyl imidazoline, chloride salt, synthesized according to the method of Wanzlick et al. (1961) *Angew. Chem.* 73:493 and Wanzlick et al. (1962) *Angew. Chem.* 74:128, and Wanzlick et al. (1963) *Chem. Ber.* 96:3024; 1,3,5-tribenzyl-[1,3,5] triazinane, synthesized according to the method of Arduengo et al. (1992) *J. Am. Chem. Soc.* 114:5530, cited supra.

EXAMPLE 1

Depolymerization of Poly(propylene carbonate) ($M_w=50,000$) with isolated carbene: 7 mg (0.02 mmol) of 1,3-(2,4,6-trimethylphenyl)imidazol-2-ylidene dissolved in toluene (0.6 mL), was added to a stirred mixture of 0.5 g of poly(propylene carbonate) in toluene (10 mL), under $N_2$. After stirring for 5 minutes at room temperature, 2 mL of methanol were added to the reaction mixture and the temperature was brought to 80° C. Stirring was continued for 3 hours followed by the evaporation of the solvent in vacuo. The $^1H$ and $^{13}C$ NMR spectra showed the presence of a single monomer, 4-methyl-[1,3]-dioxolan-2-one. However, there were 4 peaks in the GC-MS.

GC-MS:
a) m/z (5%) 5.099 min=106 (42), 103 (5), 91 (100), 77 (8), 65 (8)
b) m/z (5%) 5.219 min=106 (60), 105 (30), 103 (8), 91 (100), 77 (8), 65 (5), 51 (5)
c) m/z (85%) 6.750 min=102 (15), 87 (40), 58 (20), 57 (100). Major product.
d) m/z (5%) 9.030 min=136 (10), 135 (100), 134 (70), 120 (85), 117 (8), 103 (5), 91 (14), 77 (10), 65 (5).
$^1$H NMR: 1.4 (d, 3H), 3.9 (t, 1H), 4.5 (t, 1H), 4.8 (m, 1H).
$^{13}$C NMR: 18.96, 70.42, 73.43, 154.88

EXAMPLE 2

Depolymerization of Poly(Bisphenol A carbonate) ($M_w$=65,000) with isolated carbene: 7 mg (0.02 mmol) of 1,3-(2,4,6-trimethylphenyl)imidazol-2-ylidine dissolved in toluene (1 mL), was added to a stirred mixture of 0.5 g of poly(bisphenol A carbonate) in toluene (10 mL), under $N_2$. After stirring for 5 minutes at room temperature, 2 mL of methanol were added to the reaction mixture. The temperature was brought to 80° C. and stirring was continued for 18 hours followed by the evaporation of the solvent in vacuo. The $^1$H and $^{13}$C NMR spectra showed the presence of two compounds identified as, bisphenol A and carbonic acid 4-[1-hydroxy-phenyl)-1-methyl-ethyl]-phenyl ester 4-[1-(4-methoxy-phenyl)-1-methyl-ethyl]phenyl ester. However, GC-MS indicated 4 peaks.

GC-MS:
a) m/z (5%) 5.107 min=106 (40), 103 (5), 91 (100), 77 (8), 65 (8), 51 (8)
b) m/z (5%) 5.210 min=106 (60), 105 (30), 103 (8), 91 (100), 77 (8), 65 (5), 51 (5)
c) m/z (60%) 14.301 min=228 (30), 213 (100), 119 (15), 91 (10). Major product
d) m/z (30%) 16.016 min=495 (30), 333 (10), 319 (20), 299 (5), 281 (5), 259 (25), 239 (38), 197 (40), 181 (12), 151 (12), 135 (100), 119 (10), 91 (10).
$^1$H NMR: 1.6–1.8 (m), 2,4 (s), 3.96 (s), 6.7–6.8 (t), 7.0–7.3 (m).

EXAMPLE 3

Depolymerization of Poly(1,4-butylene adipate) ($M_n$=12,000) with isolated carbene: 0.006 g (0.02 mmol) of 1,3-(2,4,6-trimethylphenyl)imidazol-2-ylidine dissolved in toluene (1 mL), was added to a stirred mixture of 1.0 g of poly(1,4-butylene adipate) in toluene (10 mL), under $N_2$. After stirring for 5 minutes at room temperature, 2 mL of methanol were added to the reaction mixture. The temperature was brought to 80° C. and stirring was continued for 6 hours followed by the evaporation of the solvent in vacuo. The $^1$H and $^{13}$C NMR showed the presence of a single product, and the GC-MS showed two products.

GC-MS:
a) m/z (95%) 5.099 min=143 (80), 142 (20), 115 (20), 114 (100), 111 (70), 101 (65), 87 (12), 83 (25), 82 (12), 74 (36), 73 (26), 69 (10), 59 (72), 55 (60). Major product.
b) m/z (5%) 12.199 min=201 (4), 161 (6), 143 (100), 129 (32), 116 (12), 115 (25), 111 (70), 101 (12), 87 (10), 83 (15), 73 (34), 71 (12), 59 (14), 55 (42).
$^1$H NMR :1.67 (m), 2.32 (s), 4.08 (s).
$^{13}$C NMR: 24.26, 25.18, 33.74, 63.75, 173.23

EXAMPLE 4

Depolymerization of Poly(propylene carbonate) ($M_w$=50,000) with in-situ carbene: To a mixture of 7 mg (0.047 mmol) of 1-ethyl-3-methyl-1-H-imidazolium chloride in tetrahydrofuran (THF) was added 4 mg (0.038 mmol) of potassium t-butoxide (t-BOK), under $N_2$. After 30 min stirring, 0.1 mL of the reaction mixture was transferred to a flask that was charged with 0.5 g of poly(propylene carbonate) in 10 mL of THF. The reaction mixture was stirred for 10 min at room temperature followed by the addition of 2 mL of methanol. Stirring was continued at room temperature for 3 hours. Solvent was removed and the $^1$H and $^{13}$C NMR spectra showed the presence of a single product, 4-methyl-[1,3]-dioxolan-2-one. However, before the removal of the solvent the GC-MS of the crude reaction mixture showed 6 different compounds.

GC-MS:
a) m/z (15%) 6.268 min=119 (4), 90 (100), 75 (4), 59 (25).
b) m/z (5%) 6.451 min=104 (40), 103 (30), 90 (5), 77 (5), 59 (100), 58 (10), 57 (10).
c) m/z (70%) 6.879 min=102 (10), 87 (25), 58 (14), 57 (100). Major product.
d) m/z (1%) 7.565 min=103 (40), 89 (5), 59 (100), 58 (5), 57 (8).
e) m/z (4%) 8.502 min=207 (14), 133 (10), 103 (35), 90 (10), 89 (10), 59 (100) 58 (12), 57 (14).
f) m/z (5%) 8.936 min=148 (8), 118 (8), 117 (15), 103 (20), 77 (60), 72 (8), 59 (100), 58 (5), 57 (5).
$^1$H NMR: 1.4 (d, 3H), 3.9 (t, 1H), 4.5 (t, 1H), 4.8 (m, 1H).
$^{13}$C NMR: 18.96, 70.42, 73.43, 154.88

EXAMPLE 5

Depolymerization of Poly(bisphenol A carbonate) ($M_w$=65,000) with in situ carbene: To a mixture of 7 mg (0.047 mmol) of 1-ethyl-3-methyl-1-H-imidazolium chloride in THF (1 mL) was added 4 mg (0.038 mmol) of t-BOK, under $N_2$. After 30 min, stirring 0.1 mL of the reaction mixture was transferred to a flask that was charged with 0.5 g of poly(bisphenol A carbonate) in 10 mL of THF. The reaction mixture was stirred for 10 min at room temperature followed by the addition of 2 mL of methanol. Stirring was continued at room temperature for 3 hours. The solvent was removed in vacuo and the $^1$H, $^{13}$C NMR and GC-MS spectra showed a mixture of monomer and oligomers, where the major product was bisphenol A.

GC-MS:
a) m/z (10%) 12.754 min=212 (30), 198 (20), 197 (100), 182 (10), 181 (10), 179 (10), 178 (10), 165 (8), 152 (8), 135 (10), 119 (12), 103 (15), 91 (12), 77 (10), 65 (5).
b) m/z (5%) 13.674 min=282 (5), 281 (10), 255 (8), 229 (10), 228 (40), 214 (20), 213 (100), 208 (30), 197 (30), 191 (5), 181 (5), 179 (5), 165 (10), 152 (8), 135 (25), 134 (25), 133 (5), 120 (5), 119 (50), 115 (10), 103 (10), 99 (5), 97 (5), 96 (5), 91 (30), 79 (5), 77 (10), 65 (8).
c) m/z (35%) 14.286 min=228 (34), 214 (20), 213 (100), 197 (5), 165 (5), 135 (5), 119 (20), 107 (5), 91 (10), 77 (5), 65 (5). Major Product.
d) m/z (35%) 15.189 min=286 (20), 272 (15), 271 (100), 227 (5), 212 (5), 197 (3), 183 (2), 169 (3), 133 (3), 119 (5).
e) m/z (10%) 15.983 min=344 (20), 330 (20), 329 (100), 285 (5), 269 (3), 226 (3), 211 (2), 183 (3), 165 (3), 153 (2), 133 (6), 121 (2), 91 (2), 77 (1), 59 (3).

Depolymerization of PET according to the above scheme: 20 mg of t-BOK and 45 mg of N,N-diphenyl imidazoline, chloride salt, were placed in a vial with 2 mL THF and stirred for 15 minutes. Ethylene glycol (2.3 g) and PET (0.25 g) (pellets obtained from Aldrich dissolved in CHCl$_3$ and trifluoroacetic acid and precipitated with methanol to form a white powder) were combined to form a PET slurry. The catalyst was added to the slurry with approximately 5 additional mL THF. After 2 hours, the solution became more transparent, indicating dissolution of the components of the depolymerization mixture. The admixture was stirred overnight, yielding a completely clear solution the following day. the THF was removed, yielding 225 mg of white solid. $^1$H NMR $^{13}$C NMR, and GC-MS were all consistent with bis(hydroxy ethylene) terephthalate.

Depolymerization of PET according to the above scheme: 25 mg of 1,3-dimethyl imidazole, iodide salt, and 11 mg of t-BOK were placed in a vial with 2 mL of THF and stirred for 15 min. Methanol (3.11 g) and PET (308 mg, as in Example 6) were combined with 5 mL of THF to form an insoluble mixture. The catalyst mixture was filtered into the PET/methanol mixture. After 1 hour, there was a noticeable increase in transparency. After 14 hours, the solution was completely homogeneous and clear. The solvent was removed by rotary evaporation to yield a white crystalline product (250 mg). $^1$H NMR indicated complete conversion to dimethyl terephthalate.

Examples 6 and 7 may be better understood by reference to the synthetic route used to prepare the PET and the possible depolymerization products obtained therefrom. The PET obtained in each example was prepared by synthesis according to a two-step transesterification process from dimethyl terephthalate (DMT) and excess ethylene glycol (EO) in the presence of a metal alkanoate or acetate of calcium, zinc, manganese, titanium etc. The first step generates bis(hydroxy ethylene) teraphthalate (BHET) with the elimination of methanol and the excess EO. The BHET is heated, generally in the presence of a transesterification catalyst, to generate high polymer. This process is generally accomplished in a vented extruder to remove the polycondensate (EO) and generate the desired thermoformed object from a low viscosity precursor. The reaction takes place according to the following scheme:

The different options for chemical recycling are regeneration of the base monomers (DMT and EG), glycolysis of PET back to BHET, decomposition of PET with propylene glycol and reaction of the degradation product with maleic anhydride to form "unsaturated polyesters" for fiber reinforced composites and decomposition with glycols, followed by reaction with dicarboxylic acids to produce polyols for urethane foam and elastomers.

Figure 1:
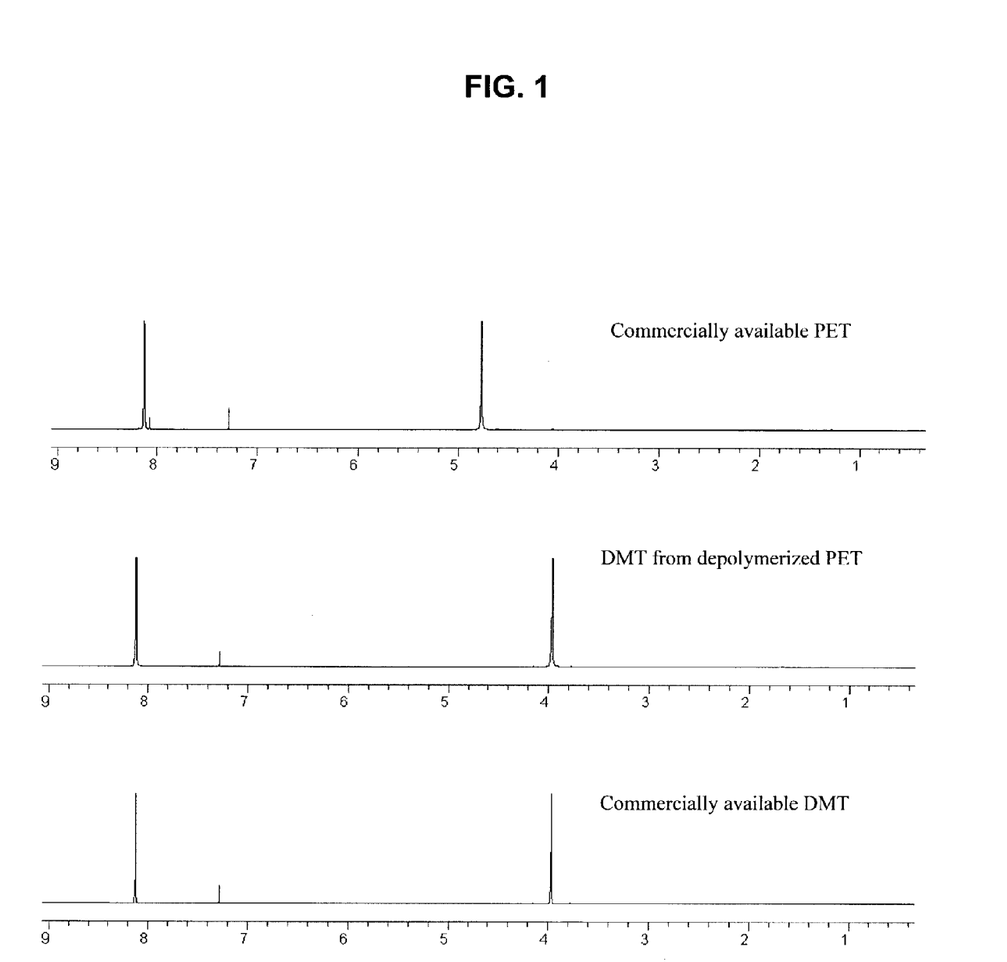
FIG. 1 illustrates the organocatalytic depolymerization of PET in the presence of excess methanol using N-heterocyclic carbene catalyst, as evaluated in Example 7.
Figure 2:
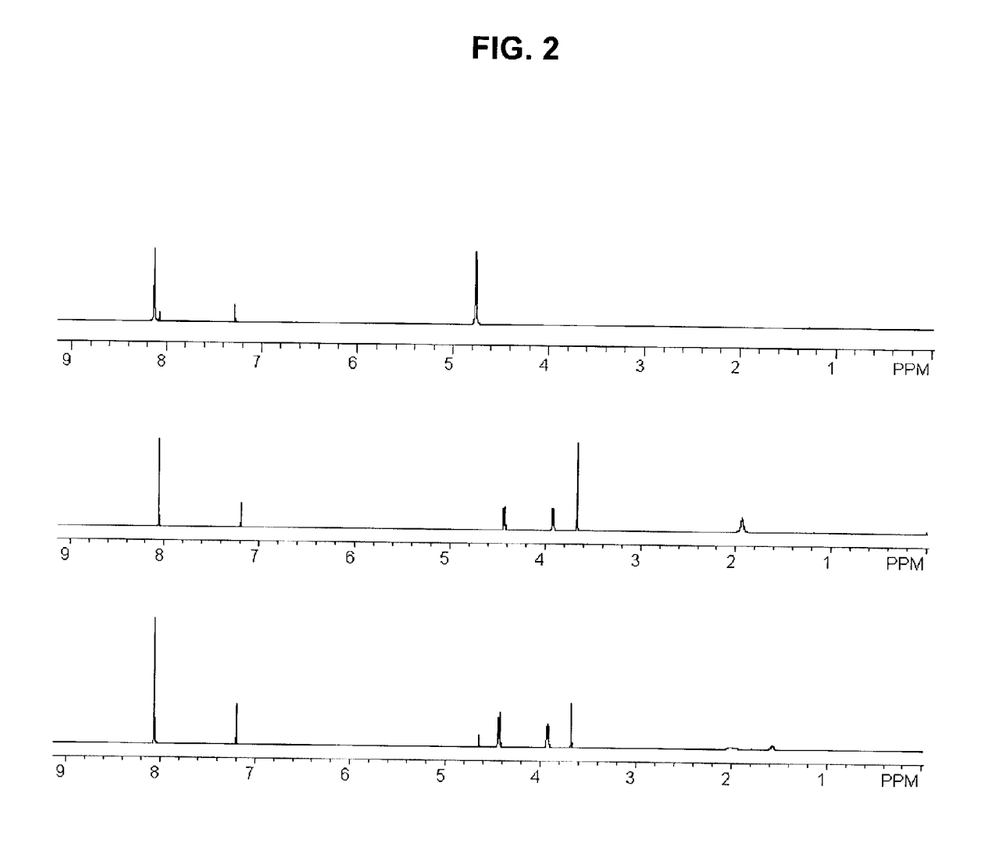
FIG. 2 illustrates the organocatalytic depolymerization of PET in the presence of ethylene glycol using N-heterocyclic carbene catalyst, as evaluated in Example 6.

In Example 7, PET powder was slurried in a THF/methanol solvent mixture. N-heterocyclic carbene (3–5 mol %), generated in situ, was added and within approximately 3 hours the PET went into solution. Anaylsis of the degradation product indicated quantitative consumption of PET and depolymerization via transesterification to EO and DMT. The DMT is readily recovered by recrystallization, while EO can be recovered by distillation (FIG. 1). Alternatively, and as established in Example 6, if EO is used as the alcohol (~50 to 200 mol % excess) in the THF slurry, the depolymerization product is BHET, which is the most desirable and can be directly recycled via conventional methods to PET (FIG. 2). The N-heterocyclic carbene catalyst platform is extremely powerful, as the nature of the substituents has a pronounced effect on catalyst stability and activity towards different substrates.

The PET depolymerization reactions of Examples 6 and 7 are illustrated schematically below.

The following Examples 8–11 describe synthesis of new carbene precursors as illustrated in the following scheme:

EXAMPLE 8

3-Benzyl-1-methoxy-4,5-dimethylimidazolium iodide (2): Methyl iodide (0.5 mL, 7.8 mmol) was added via syringe to a solution of imidazole-N-oxide 1 (1.0 g, 4.9 mmol) in ca. 20 mL of $CHCl_3$ (compound 1 was prepared from 1,3,5-tribenzyl-[1,3,5]triazinane and butane-2,3-dione monooxime using the procedure of Arduengo et al. (1992), supra.) The resulting mixture was stirred at room temperature overnight. Removal of the volatiles in vacuo afforded a thick yellow oil of suitable purity in an undetermined yield.

$^1$H-NMR ($\delta$, $CDCl_3$): 10.32 (s, 1H, N—CH—N); 7.39 (m, 5H, $C_6H_5$); 5.56 (s, 2H, $NCH_2$); 4.38 (s, 3H, $OCH_3$); 2.27 (s, 3H, $CH_3$); 2.20 (s, 3H, $CH_3$).

EXAMPLE 9

3-Benzyl-1-methoxy-4,5-dimethylimidazolium hexafluorophosphate (3): Crude iodide 2 was taken up in deionized (DI) water, which separated the product from small amounts of a dark, insoluble residue. The water solution was decanted to a second flask and a solution of ammonium hexafluorophosphate (950 mg, ca. 5.8 mmol) in 10 mL of DI water was added in portions. An oil separated during the addition, and the supernatant solution was decanted out. The oil was crushed in cold (0° C.), and subsequently recrystallized in methanol. Yield: 1.3 g (73% from 1). $^1$H-NMR ($\delta$, $CDCl_3$): 8.67 (s, 1H, N—CH—N); 7.39 (m, 3H, $C_6H_5$); 7.29 (d, 2H, $C_6H_5$); 5.24 (s, 2H, $NCH_2$); 4.21 (s, 3H, $OCH_3$); 2.27 (s, 3H, $CH_3$); 2.17 (s, 3H, $CH_3$).

EXAMPLE 10

1-Benzyloxy-3-benzyl-4,5-dimethylimidazolium bromide (4): Benzyl bromide (1.2 mL, ca. 10 mmol) was added via syringe to a refluxing suspension of 1 (1.0 g, 5.0 mmol)

in dry benzene. A dark orange oil separated after refluxing for 6 h, and cooling to room temperature. The supernatant was decanted and the remaining oil was dried under vacuum overnight, which caused the product to solidify. The solid mass was crushed in pentane, filtered and dried under vacuum. Yield: 1.34 g (63%). $^1$H-NMR ($\delta$, CDCl$_3$): 11.04 (s, 1H, N—CH—N); 7.6–7.2 (ov. m, 10H, 2×C$_6$H$_5$); 5.59, 5.58 (s+s, N—CH$_2$, O—CH$_2$); 2.09, 1.94 (s, 3H, CH$_3$, CH$_3$). $^{13}$C-NMR ($\delta$, CDCl$_3$): 132.8 (OCH$_2$—C$_6$H$_5$); 132.5 (NCN); 131.5 (NCH$_2$—$^i$C$_6$H$_5$); 130.6, 130.3, 129.2, 129.0, 129.0, 128.9, 128.0 ($^{omp}$C$_6$H$_5$); 124.8; 124.1 (NCCN); 83.9 (OCH$_2$); 51.2 (NCH$_2$); 8.89 (CH$_3$); 7.11 (CH$_3$).

EXAMPLE 11

3-Benzyl-1-benzyloxy-4,5-dimethylimidazolium hexafluorophosphate (5): A batch of crude bromide 4 (still as an oil before drying under vacuum) was dissolved in DI water and extracted with hexanes. The aqueous layer was separated and a solution of ammonium hexafluorophosphate (ca. 1.3 equiv.) was added dropwise with constant stirring. The yellow oil deposited on the walls of the flask was dissolved in warm methanol and a few drops of hexanes were added. Cooling to room temperature afforded off-white crystals of pure 5, which were rinsed with pentane and dried under vacuum. Yield: (82% from 1). $^1$H-NMR ($\delta$, CDCl$_3$): 8.42 (s, 1H, N—CH—N); 7.45–7.35, 7.18 (ov. m, C$_6$H$_5$); 5.31, 5.20 (s+s, N—CH$_2$, O—CH$_2$); 2.13 (s, 3H, CH$_3$); 2.05 (s, 3H, CH$_3$).

Bis(1-Benzyloxy-3-benzyl-4,5-dimethylimidazolylidene) silver(I) dibromoargentate (6). The carbene precursor 6 was prepared as follows: A mixture of silver oxide (128 mg, 0.55 mmol) and imidazolium bromide 4 (396 mg, 1.06 mmol) was taken up in dry CH$_2$Cl$_2$ and stirred at room temperature for 90 minutes. The dark orange suspension was filtered through a pad of celite and evaporated to dryness, yielding an orange powder. Crystallization from THF afforded a white powder (2 crops). Yield: 291 mg (57%). $^1$H-NMR ($\delta$, CD$_2$Cl$_2$): 7.47–7.32 (ov. m, 10H, 2×CrH$_5$); 5.23, 5.22 (s+s, NCH$_2$, OCH$_2$); 2.01, 1.95 (s, 3H+3H, CH$_3$, CH$_3$). $^{13}$C-NMR ($\delta$, CD$_2$Cl$_2$): 136.2 (NCN); 133.3 (OCH$_2$—$^i$C$_6$H$_5$); 130.8 (NCH$_2$—$^i$C$_6$H$_5$); 130.7, 130.0; 129.3, 129.3, 128.5, 127.1, 123.9 ($^{omp}$C$_6$H$_5$+NCCN); 82.6 (OCH$_2$); 54.0 (NCH$_2$); 9.4 (CH$_3$); 7.8 (CH$_3$). Anal. Found: C, 47.56; H, 4.26; N, 5.79%. Calc. for C$_{38}$H$_{40}$Ag$_2$Br$_2$N$_4$O$_2$: C, 47.53; H, 4.20;; N, 5.83%.

Examples 13 and 14 describe preparation of additional carbene precursors from N,N-diaryl-substituted diamines as illustrated in the schemes below.

Synthesis of carbene precursor 7 (2-pentafluorophenyl-1,3-diphenyl-imidazolidine): 200 mg (0.94 mmol, FW=212.12) N,N'-diphenyl-ethane-1,2-diamine was placed in a vial and dissolved in 5mL CH$_2$Cl$_2$. A catalytic amount of p-toluenesulfonic acid and 50 mg of Na$_2$SO$_4$ were added, followed by 230 mg (0.94 mmol, FW=196.07) of pentafluorobenzaldehyde. The mixture was stirred for 8 h. The Na$_2$SO4 was filtered off and solvent was removed under reduced pressure to yield a light brown powder 395 mg (FW=436.2), 96% yield. $^1$H NMR: (400 MHz, CDCl$_3$, 25° C.) $\delta$=3.7–3.9 (m, 2H), 3.9–4.1 (m, 2H), 6.5 (s, 1H), 6.7–6.8 (m, 2H), 6.8–6.9 (m, 1H), 7.2–7.5 (m, 2H). $^{19}$F NMR: $\delta$=−143.2 (s br, 2F), −153.7–153.8 (m, 1F), 161.7–161.8 (m, 2F).

-continued

8

Synthesis of carbene precursor 8 (2-pentafluorophenyl-1,3-bis-(2,4,6-trimethyl-phenyl)-imidazolidine): Mesityl-diamine (512 mg, 1.7 mmol) was placed into a vial, equipped with a stirbar, with pentafluorobenzaldehyde (340 mg, 1.7 mmol). Glacial acetic acid (5 mL) was added and the reaction was stirred at room temperature for 24 h. The acetic acid was removed under reduced pressure and the product was washed several times with cold methanol to afford the product as a white crystalline solid (543 mg, 65%). $^1$H NMR: (400 MHz, CDCl$_3$, 25° C.) δ: 2.2 (s, 12H), 2.3 (s, 6H), 3.5–3.6 (m, 2H), 3.9–3.4 (m, 2H), 6.4 (s, 1H), 6.9 (s, 4H). $^{19}$F NMR: −136.3–136.4 (m, 1F), −148.6–148.7 (m, 1F), −155.8–155.9 (m, 1F), −163.0–163.3 (m, 2F).

We claim:

1. A heteroatom-stabilized carbene having the structure of formula (I)

wherein:
E$^1$ and E$^2$ are independently selected from N, NR$^E$, P, and PR$^E$, R$^E$ is hydrogen, heteroalkyl, or heteroaryl, x and y are independently zero, 1, or 2, and are selected to correspond to the valence state of E$^1$ and E$^2$, respectively, and E$^1$ and E$^2$ are linked through a linking moiety that provides a heterocyclic ring in which E$^1$ and E$^2$ are incorporated as heteroatoms;
R$^1$ and R$^2$ are independently selected from branched C$_3$–C$_{30}$ hydrocarbyl, substituted branched C$_3$–C$_{30}$ hydrocarbyl, heteroatom-containing branched C$_4$–C$_{30}$ hydrocarbyl, substituted heteroatom-containing branched C$_4$–C$_{30}$ hydrocarbyl, cyclic C$_5$–C$_{30}$ hydrocarbyl, substituted cyclic C$_5$–C$_{30}$ hydrocarbyl, heteroatom-containing cyclic C$_1$–C$_{30}$ hydrocarbyl, and substituted heteroatom-containing cyclic C$_1$–C$_{30}$ hydrocarbyl;
L$^1$ and L$^2$ are linkers containing 1 to 6 spacer atoms, and are independently selected from heteroatoms, substituted heteroatoms, hydrocarbylene, substituted hydrocarbylene, heteroatom-containing hydrocarbylene, and substituted heteroatom-containing hydrocarbylene; and
m and n are independently zero or 1,
with the proviso that a heteroatom is directly bound to E$^1$, E$^2$, or to both E$^1$ and E$^2$.

2. The carbene of claim 1, wherein E$^1$ is NR$^E$.

3. The carbene of claim 2, wherein R$^E$ is alkoxy, substituted alkoxy, aryloxy, substituted aryloxy, aralkoxy, or substituted aralkoxy.

4. The carbene of claim 3, wherein R$^E$ is lower alkoxy or monocyclic aryl-substituted lower alkoxy.

5. The carbene of claim 3, wherein:
E$^2$ is N;
x is zero;
y is 1; and
E$^1$ and E$^2$ are linked through a substituted or unsubstituted lower alkylene or lower alkenylene linkage.

6. The carbene of claim 5, wherein:
E$^1$ and E$^2$ are linked through a moiety —CR$^3$R$^4$—CR$^5$R$^6$— or —CR$^3$=CR$^5$—, wherein R$^3$, R$^4$, R$^5$, and R$^6$ are independently selected from hydrogen, halogen, and C$_1$–C$_{12}$ alkyl;
n is 1;
L$^2$ is lower alkylene; and
R$^2$ is monocyclic aryl or substituted monocyclic aryl.

7. The carbene of claim 6, wherein E$^1$ and E$^2$ are linked through a moiety —CR$^3$=CR$^5$—.

8. The carbene of claim 7, wherein R$^3$ and R$^5$ are hydrogen.

9. The carbene of claim 7, wherein R$^3$ and R$^5$ are C$_1$–C$_{12}$ alkyl.

10. The carbene of claim 9, wherein R$^3$ and R$^5$ are methyl.

11. The carbene of claim 4, wherein:
E$^2$ is N;
x is zero;
y is 1; and
E$^1$ and B$^2$ are linked through a substituted or unsubstituted lower alkylene or lower alkenylene linkage.

12. The carbene of claim 11, wherein:
E$^1$ and E$^2$ are linked through a moiety —CR$^3$R$^4$—CR$^5$R$^6$— or —CR$^3$=CR$^5$—, wherein R$^3$, R$^4$, R$^5$, and R$^6$ are independently selected from hydrogen, halogen, and C$_1$–C$_{12}$ alkyl;
n is 1;
L$^2$ is lower alkylene; and
R$^2$ is monocyclic aryl or substituted monocyclic aryl.

13. The carbene of claim 12, wherein E$^1$ and E$^2$ are linked through a moiety —CR$^3$=CR$^5$—.

14. The carbene of claim 13, wherein R$^3$ and R$^5$ are hydrogen.

15. The carbene of claim 13, wherein R$^3$ and R$^5$ are C$_1$–C$_{12}$ alkyl.

16. The carbene of claim 15, wherein R$^3$ and R$^5$ are methyl.

17. The carbene of claim 16, wherein R$^E$ is methoxy.

18. The carbene of claim 17, wherein L$^2$ is methylene and R$^2$ is phenyl.

19. The carbene of claim 16, wherein R$^E$ is benzyloxy.

20. The carbene of claim 19, wherein L$^2$ is methylene and R$^2$ is phenyl.

21. The carbene of claim 1, wherein x and y are 1, and E$^1$ and E$^2$ are N and linked through a moiety L, such that the carbene has the structure of formula (II)

wherein:
L is the linking moiety, and is selected from a hydrocarbylene, substituted hydrocarbylene, heteroatom-containing hydrocarbylene, and substituted heteroatom-containing hydrocarbylene linker, wherein two or more substituents on adjacent atoms within L may be linked to form an additional cyclic group;

one of $L^1$ and $L^2$ is lower alkylene and the other is O; and m and n are independently zero or 1.

22. The carbene of claim 1, wherein L is —$CR^3R^4$—$CR^5R^6$— or —$CR^3{=}CR^5$—, wherein $R^3$, $R^4$, $R^5$, and $R^6$ are independently selected from hydrogen, halogen, $C_1$–$C_{12}$ alkyl, or wherein any two of $R^3$, $R^4$, $R^5$, and $R^6$ may be linked together to form a substituted or unsubstituted, saturated or unsaturated ring, such that the N-heterocyclic carbene has the structure of formula (III)

(III)

in which q is an optional double bond, s is zero or 1, and t is zero or 1, with the proviso that when q is present, s and t are zero, and when q is absent, s and t are 1.

23. The carbene of claim 22, wherein $R^1$ and $R^2$ are independently selected from secondary $C_3$–$C_{12}$ alkyl, tertiary $C_4$–$C_{12}$ alkyl, $C_5$–$C_{12}$ aryl, substituted $C_5$–$C_{12}$ aryl, $C_6$–$C_{18}$ alkaryl, substituted $C_6$–$C_{18}$ alkaryl, $C_5$–$C_{12}$ alicyclic, and substituted $C_5$–$C_{12}$ alicyclic.

24. The carbene of claim 23 wherein $R^1$ and $R^2$ are independently selected from $C^5$–$C_{12}$ aryl, mono-, di, and tri-lower alkyl-substituted $C_5$–$C_{12}$ aryl, $C_6$–$C_{12}$ alkaryl, and mono-, di, and tri-lower alkyl-substituted $C_6$–$C_{12}$ alkaryl, and $R^3$ and $R^4$ are hydrogen.

25. A carbene precusor having the structure of formula (PI)

(PI)

wherein:

$E^1$ and $E^2$ are independently selected from N, $NR^E$, P, and $PR^E$, $R^E$ is hydrogen, heteroalkyl, or heteroaryl, x and y are independently zero, 1, or 2, and are selected to correspond to the valence state of $E^1$ and $E^2$, respectively, and $E^1$ and $E^2$ are linked through a linking moiety that provides a heterocyclic ring in which $E^1$ and $E^2$ are incorporated as heteroatoms;

$R^1$ and $R^2$ are independently selected from branched $C_3$–$C_{30}$ hydrocarbyl, substituted branched $C_3$–$C_{30}$ hydrocarbyl, heteroatom-containing branched $C_4$–$C_{30}$ hydrocarbyl, cyclic $C_5$–$C_{30}$ hydrocarbyl, substituted cyclic $C_5$–$C_{30}$ hydrocarbyl, heteroatom-containing cyclic $C_1$–$C_{30}$ hydrocarbyl, and substituted heteroatom-containing cyclic $C_1$–$C_{30}$ hydrocarbyl;

$L^1$ and $L^2$ are linkers containing 1 to 6 spacer atoms, and are independently selected from heteroatoms, substituted heteroatoms, hydrocarbylene, substituted hydrocarbylene, heteroatom-containing hydrocarbylene, and substituted heteroatom-containing hydrocarbylene; and m and n are independently zero or 1, with the proviso that a heteroatom is directly bound to $E^1$, $E^2$, or to both $E^1$ and $E^2$.

26. A carbene precursor having the structure of formula (PII)

(PII)

wherein:

$E^1$ and $E^2$ are independently selected from N, $NR^E$, P, and $PR^E$, $R^E$ is hydrogen, heteroalkyl, or heteroaryl, x and y are independently zero, 1, or 2, and are selected to correspond to the valence state of $E^1$ and $E^2$, respectively, and $E^1$ and $E^2$ are linked through a linking moiety that provides a heterocyclic ring in which $E^1$ and $E^2$ are incorporated as heteroatoms;

$R^1$ and $R^2$ are independently selected from branched $C_3$–$C_{30}$ hydrocarbyl, substituted branched $C_3$–$C^{30}$ hydrocarbyl, heteroatom-containing branched $C_4$–$C_{30}$ hydrocarbyl, substituted heteroatom-containing branched $C_4$–$C_{30}$ hydrocarbyl, cyclic $C_5$–$C_{30}$ hydrocarbyl, substituted cyclic $C_5$–$C_{30}$ hydrocarbyl, heteroatom-containing cyclic $C_1$–$C_{30}$ hydrocarbyl, and substituted heteroatom-containing cyclic $C_1$–$C_{30}$ hydrocarbyl;

$L^1$ and $L^2$ are linkers containing 1 to 6 spacer atoms, and are independently selected from heteroatoms, substituted heteroatoms, hydrocarbylene, substituted hydrocarbylene, heteroatom-containing hydrocarbylene, and substituted heteroatom-containing hydrocarbylene;

m and n are independently zero or 1,

M is a metal;

Ln is a neutral or anionic ligand; and j is the number of ligands bound to M, wherein when j is greater than 1, the Ln may be the same or different, with the proviso that a heteroatom is directly bound to $E^1$, $E^2$, or to both $E^1$ and $E^2$.

* * * * *

UNITED STATES PATENT AND TRADEMARK OFFICE
CERTIFICATE OF CORRECTION

PATENT NO. : 7,053,221 B2
APPLICATION NO. : 10/355554
DATED : May 30, 2006
INVENTOR(S) : James Lupton Hedrick, Gregory Walker Nyce and Robert M. Waymouth It is certified that error appears in the above-identified patent and that said Letters Patent is hereby corrected as shown below:

Claim 11 (col. 24, line 28):   "$B^2$" should be --$E^2$--;

Claim 21 (col. 25, line 7):   "$CR5$" should be --$CR^5$--;

Claim 23 (col. 25, line 29):   "$C^{18}$" should be --$C_{18}$--;

Claim 24 (col. 25, line 32):   "$C^5$" should be --$C_5$--;

Claim 25 (col. 26, line 2):   "heteroatom-containing branched $C_4$-$C_{30}$ hydrocarbyl," should be followed by --substituted heteroatom-containing branced $C_4$-$C_{30}$ hydrocarbyl,--; and Claim 26 (col. 26, line 33):   "$C^{30}$" should be --$C_{30}$--.

Signed and Sealed this

Seventh Day of November, 2006

JON W. DUDAS
*Director of the United States Patent and Trademark Office*

UNITED STATES PATENT AND TRADEMARK OFFICE
CERTIFICATE OF CORRECTION

PATENT NO.         : 7,053,221 B2
APPLICATION NO.    : 10/355554
DATED              : May 30, 2006
INVENTOR(S)        : James Lupton Hedrick, Gregory Walker Nyce and Robert M. Waymouth It is certified that error appears in the above-identified patent and that said Letters Patent is hereby corrected as shown below:

Title Page
Item (73): The assignees of the subject application should be:
--International Business Machines, Armonk, N.Y. (US), and
The Board of Trustees of the Leland Stanford Junior University, Palo Alto, CA (US)--

Signed and Sealed this

Fourth Day of December, 2007

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 7,053,221 B2 | Page 1 of 1 |
| APPLICATION NO. | : 10/355554 | |
| DATED | : May 30, 2006 | |
| INVENTOR(S) | : Hedrick et al. | |

It is certified that error appears in the above-identified patent and that said Letters Patent is hereby corrected as shown below:

In the Specification Under Column 1:

• Please replace Column 1, line no. 13-19 with:

-- FEDERALLY-SPONSORED RESEARCH OR DEVELOPMENT
This invention was made with Government support under contract 9808677 awarded by the National Science Foundation. The Government has certain rights in this invention. --

Signed and Sealed this
Sixteenth Day of April, 2013

Teresa Stanek Rea
*Acting Director of the United States Patent and Trademark Office*